United States Patent [19]

Beran

[11] Patent Number: 4,861,523
[45] Date of Patent: Aug. 29, 1989

[54] HUMIDIFICATION IN RESPIRATORY SYSTEMS

[76] Inventor: Anthony V. Beran, 1472 La Loma Dr., Santa Ana, Calif. 92705

[21] Appl. No.: 72,543

[22] Filed: Jul. 13, 1987

[51] Int. Cl.⁴ ............................................... B01F 3/04
[52] U.S. Cl. .............................. 261/104; 128/204.13; 128/203.16
[58] Field of Search ...................... 128/200.11, 200.14, 128/200.18, 203.16, 203.17, 203.26, 203.27, 204.13; 261/104, DIG. 65

[56] References Cited

U.S. PATENT DOCUMENTS

| | | | |
|---|---|---|---|
| 3,432,357 | 3/1969 | Danhere | 261/104 X |
| 3,532,276 | 10/1970 | Schoen, Jr. | 261/104 |
| 3,902,486 | 9/1975 | Guichard | 128/204.13 X |
| 4,146,597 | 3/1979 | Echstein et al. | 128/204.13 X |
| 4,381,267 | 4/1983 | Jachson | 128/204.13 X |
| 4,430,994 | 2/1984 | Clawson et al. | 128/204.13 X |
| 4,705,033 | 11/1987 | Halfpenny | 128/203.26 X |
| 4,708,831 | 11/1987 | Elsworth et al. | 261/104 X |

Primary Examiner—John Fox
Attorney, Agent, or Firm—Price, Gess & Ubell

[57] ABSTRACT

Respiratory gas is humidified by flowing it along a flowpath at least a portion of whose wall is formed of a barrier material which is pervious to water vapor and impervious to water while the side of said wall opposite the flowpath is subjected to one or both of water and water vapor. Production of such a flowpath can be accomplished by compressing and bonding together selected portions of a resilient, open-celled material which is disposed as a layer between layers of water impermeable material at least one of which layers is permeable by water vapor.

6 Claims, 1 Drawing Sheet

HUMIDIFICATION IN RESPIRATORY SYSTEMS

BACKGROUND

Systems for delivering respiratory gas to patients include apparatus which serves as the source of air, oxygen and sometimes other respiratory gases, in appropriate proportion and at an appropriate positive pressure. The gas is delivered to the patient through a delivery conduit to what is sometimes called a "patient connection". The patient connection may be a mask or an intubation set, in incubator or even a tent. Particularly when the purpose of the respiratory system includes forced or paced ventilation of the patient, the system will include an exhaust conduit which extends from the patient connection to a point of negative gage pressure.

In many cases it is required that the gas be delivered to the patient connection at an elevated temperature near body temperature and that the gas be humid to the point of saturation or nearly so. Heating and humidifying are readily accomplished. However, to accomplish them in a way that minimizes discomfort and danger to the patient is seldom easy. The problem is twofold. The delivered gas must not exceed safe temperature and water, humidifying water and condensate, must not reach the patient. If humidification of the gas is accomplished at the supply apparatus or in the supply conduit at an appreciable distance from the patient connection, an excessive amount of condensate will form in the delivery conduit as the gas passes along the conduit and is cooled. If that condensate reaches the patient's mask or intubation set, the patient, an infant or comatose patient for example, may be drowned.

Temperature measurement and control is accomplished automatically with relative ease. Heating is done electrically and is readily controlled electronically. Humidification is less convenient. The conventional system employs a "bubbler", a container of water connected in the gas delivery conduit such that the gas must flow through the water. Gas from the source is conducted to a point in the bubbler below the level of the water. There it emerges into the water and bubbles up to the ullage space above the water. Still under pressure, it flows to the patient connection. Heating is accomplished at the humidifier or upstream from it for to heat it downstream would reduce the degree of humidification. Moving the humidifier downstream reduces the opportunity for condensate to form but it increases the danger that a spill in the humidifier will reach and drown the patient. In practice, the distance from the gas source to patient connection differs from case to case, patients must be free to move or be moved and, for additional reasons, the conduits and humidifier and heater are often assembled into jury rigged, temporary flow circuits. The danger that a humidifier or water trap will be dislodged from its mounting and upset to spill water to the patient side of the device is a continuing danger.

The disadvantages of the bubbler humidifier do not end with their potential for drowning patients. Because the water they use is included in the flowpath, sterile water must be used. Moreover they are noisy. The constant bubbling sound all through an otherwise quiet night can interfere with sleep and be irritating. In the case of a sedated patient, the constant sound can be stressful.

SUMMARY OF THE INVENTION

It is an object of the invention to provide an humidifier which is less hazardous than the bubbler type.

Another object is to provide an humidifier which is substantially soundless, which eliminates need for an associated water trap and which may use ordinary tap water.

A further object is to provide a reliable, high quality humidifier which is sufficiently inexpensive to produce and store to warrant disposal after use by a single patient and a related object is to provide a humidifier which may be formed of flexible materials.

A still further object is to provide an improved method for producing humidifiers for respiratory systems.

These and other objects and advantages of the invention which will become apparent upon examination of the accompanying drawings and the following specification are realized in part by confining the water of the humidifier such that only the vapors of the water enter the respiratory gas flowpath. A barrier is imposed between the water and gas which permits the flow of vapor while precluding transfer of water and bacteria.

Another feature of the invention is that the contribution of the humidifier to the compliance of the system is constant and does not change with water level whereby the invention is particularly useful in respiratory systems for infants where pressure differentials are very low or are required to change very rapidly.

THE DRAWINGS

DESCRIPTION OF THE PREFERRED EMBODIMENT

Figure 1:
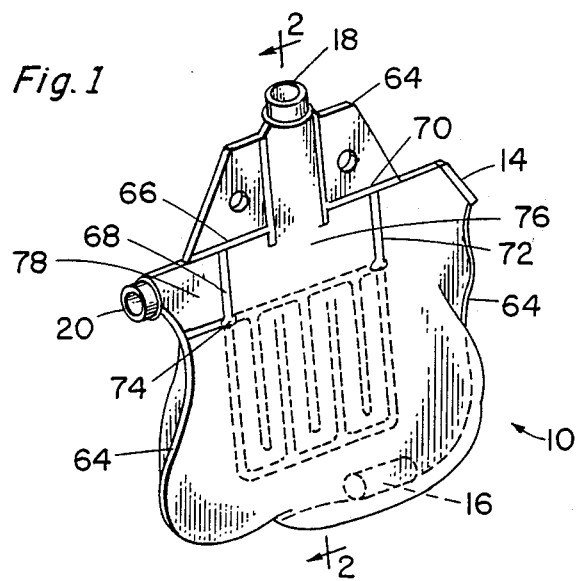
FIG. 1 is an isometric view of the currently preferred form of humidifier according to the invention shown as it appears when partially filled with water.
Figure 2:
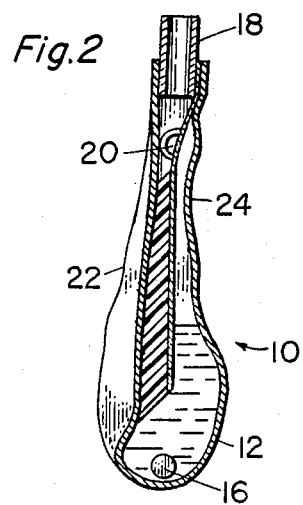
FIG. 2 is a cross sectional view taken on line 2—2 of FIG. 1.

One major advantage of the invention is that it can be embodied in a wide variety of structural forms in which spacial orientation forms is not critical. One of those forms, a form now preferred, is shown in the figures of the drawing. It is shown in assembled condition, partly filled with water and is designated 10 in FIGS. 1 and 2. The body of water is numbered 12 in FIG. 2. It is introduced into the unit at a "zip lock" seal 14 which is visible in FIG. 1. The packet 16, which lies at the bottom of the body of water and through which water flows with ease, contains any selected one of the chemicals which reacts exothermaly with water. Use of chemical heating is an optional feature of the invention. An alternative is to use an electric heater element either adjacent to the humidifier or within it. However, Chemical heating is preferred. Like the body of water the chemical container moves to the bottom of the unit in any orientation of the humidifier so it is always in water unless there is no water in which case there is no heating. Thus the system is fail safe.

Figure 3:
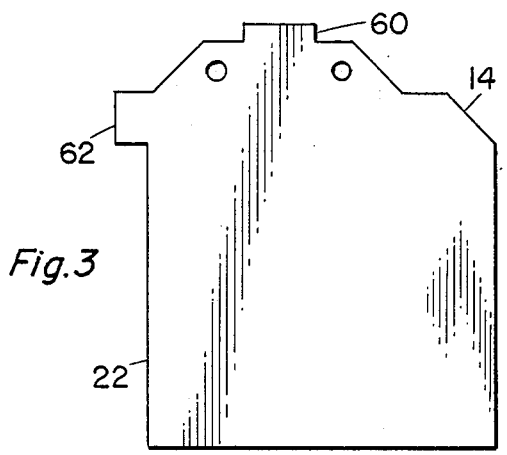
FIGS. 3 and 4 are elevational views of the front and rear side panels, respectively, of the unit of FIG. 1 in 2 unassembled condition.
Figure 4:
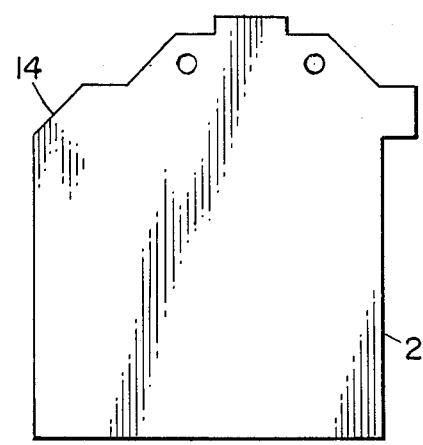
Figure 5:
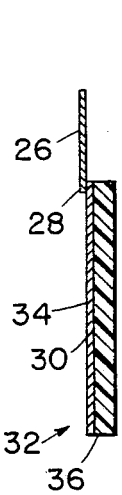
FIG. 5 is a view in front elevation of the air labyrinth sub assembly.
Figure 6:
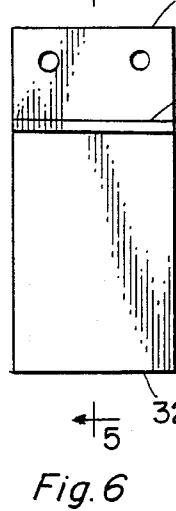
FIG. 6 is a front elevational view of the assembled combination of the front side panel and the sub assembly of FIG. 5.

The numeral 18 identifies the inlet tube, and the numeral 20 identifies the outlet tube, for respiratory gas. The other components of the unit are shown in FIGS. 3, 4, 5 and 6. All are transparent in the preferred form. The front wall 22 and rear wall 24 are formed of pliant sheets of plastic. The inner side of those walls is shown in FIGS. 3 and 4, respectively. The labyrinth assembly is seen in FIGS. 5 and 6 to comprise a rectangular sheet of plastic 26 whose lower edge is bonded at 28 over its entire length to the upper edge at the rear layer 30 of a foam sandwich 32. The front layer of the sandwich is designated 34 and the intermediate foam layer is designated 36. All of the components are formed of "medically safe" plastics which can be bonded by a convenient process such, for example, as sonic welding or radio frequency bonding. All are impervious to water. The walls of the sandwich member 32, at least the rear wall 30, are made of a gas permeable material through which water vapor flows with ease. The foam layer 36 is open celled such that it permits the flow of respiratory gas therethrough with little resistance. In this embodiment the sides 22 and 24 are formed of polyvinyl chloride. The foam 36 is an open celled, resilient polyurathane. Open celled, resilient vinyl foam is equally useful. The rear face 30 of the foam sandwich is formed by a layer of porus teflon which may be bonded to the foam 36 at one side and is covered by a layer of polyester support material at its other side. The rectangular piece 26 is made of polyvinyl chloride material.

Figure 8:
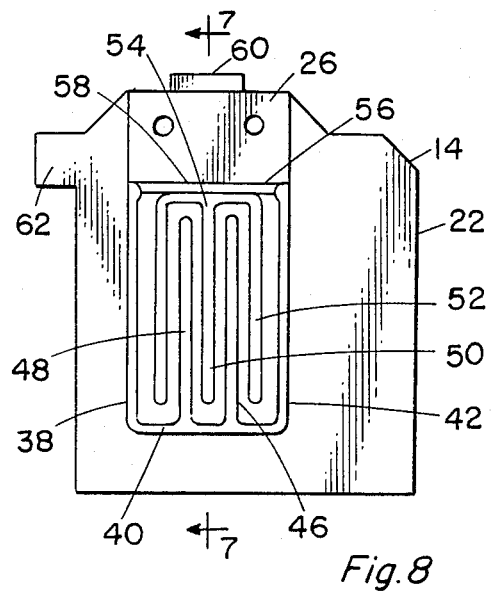
FIG. 8 is a cross sectional view taken on line 8—8 of FIG. 6.

It is possible by compressing the foam 36 and applying bonding energy along a given line or area, as by heating or ultrasonic welding, to form a barrier against the flow of gas through the foam 36 from one portion of the sandwich to another. That is done in the invention preferably by sonic welding. The sandwich 32 is compressed and welded, as best shown in FIG. 8, along lines that define a labyrinth through which may flow from an inlet to an outlet. In this embodiment the weld lines 38, 40 and 42 form a barrier to gas flow along the side and bottom edges of the foam sandwich 32. Vertical weld lines 44 and 46 divide the area of the sandwich into three parts. The legs 48, 50 and 52 of the M-shaped weld line 54 extend into those three parts and divide them to confine flow to an inlet 56 for flow and a flowpath including five direction reversals to an outlet at 58. The dashed lines across inlet 56 and outlet 58 represent the weld line 28 best shown in FIG. 5.

The structure which results from formation of those weld lines, or bond lines if another bonding process is used, will permit a ready flow of respiratory gas along the labyrinth of foam. The outer wall or coating of porus plastic permits water vapor to flow into the foam passageway through the porus wall while precluding the flow of water into the foam passageway. Respiratory gas can flow through the porus wall out of the passageway and that occurs until the partial pressure of respiratory gas outside the sandwich equals the partial pressure of that gas inside the flowpath. The sandwich structure is confined in a container for water which container is impervious to both gas and water. When the partial pressure of respiratory gas in the ullage space of the container rises to the partial pressure in the flowpath, no more respiratory gas escapes from the flowpath to the ullage space. That loss is insignificant because the water container is designed to contain all of that portion of the respiratory gas flowpath which has a gas pervious wall.

Figure 7:
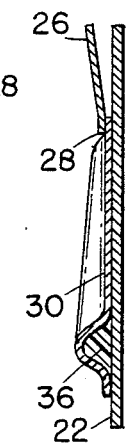
FIG. 7 is a cross sectional view 5 taken on line 7—7 of FIG. 5.

In addition to containing the gas pervious part of the flowpath, the preferred embodiment of the invention provides an impervious port structure for conducting gas to and from the pervious portion of the path and the port structure is formed integrally with the water container. The subassembly 32 is placed on one of the water container walls 22 or 24 as shown in FIG. 8 with the extension portion 26 at the side away from the water container wall, in this case wall 22. It is placed such that the extension 26 overlies the portion of the container wall adjacent to, and below both sides of, the part 60 of the water container wall which is to be bonded to the inlet port tube. It is convenient to bond the subassembly 32 to the water container wall to insure the subassembly is properly positioned during the remainder of the assembly process. To that end the subassembly is bonded to the wall 22 in the step of forming the bond lines that define the flowpath labyrinth. Thus, in this embodiment the subassembly 32 and wall 22 are joined along bond lines 38 through 54 as best shown in FIG. 7. The result is that the surface of the flowpath at the side toward wall 22 is foreclosed from exposure to the water and ullage space of the water container in the final assembly. In alternate designs the subassembly is bonded to the water container walls only at extension 26 or not at all prior to final assembly.

Assembly is completed by positioning inlet and outlet tubes 18 and 20 so they overlie parts 60 and 62, respectively, of wall 22. Tube 18 is placed between wall 22 and the extension 26. The other wall 24 of the water container is placed over wall 22 and the tubes 18 and 20 and subassembly 32 edge to edge with wall 22. The margins of walls 22 and 24 are bonded to the inlet and outlet tubes and to the upper margin of extension 26 and to one another, except at the "zip lock" area 14 to form a container for water which is sealed when the "zip lock" is closed. The marginal bond is numbered 64 in the drawing at FIG. 1. In addition, the walls 22 and 24 and extension are bonded together at lines 66, 68, 70 and 72 in FIG. 1. Those bond lines extend from the marginal bond 64 to the bond line 28 by which the foam sandwich is fixed to extension 26. Another bond line 74 extends from marginal bond 64 to bond line 28 and joins wall 22 to wall 24. Those several bond lines divide the upper portion of the final assembly into a compartment 76 which defines a flow path from inlet tube 18 to the labyrinth inlet 56 and a compartment 78 which defines a flowpath from the labyrinth outlet 58 to outlet tube 20. Walls 22 and 24 form the walls of compartment 78. Wall 22 and extension 26 form the walls of compartment 76.

Water and the heater chemical, if any, are introduced into the water container at "zip lock" 14. When closed the "zip lock" forms a seal against loss of water or gas. There is a complete exclusion of water from the respiratory gas flowpath. Those factors, coupled with the fact that the ullage space in the water container will be filled with water vapor and the fact that water vapor passes through the porus wall of the labyrinth both from the water and from the ullage space, permit humidification of respiratory gas which flows along the flowpath efficiently and in equal degree regardless of the spacial orientation of the unit or the amount of water in the container except when the container is empty of water.

Because the water and any heater chemical will move together to the lowest part of the container in any orientation, the chemical is simply inserted into the container. No mounting or special placement is required. Because the labyrinth wall is impervious to bacteria, there is no requirement that the water be sterilized. The only real limitation is that the reaction of the heater chemical with water produce no substance which is both harmful and capable of penetrating into the respiratory gas flowpath.

It will be apparent that the flowpath need not be a labyrinth of the shape shown or even a labyrinth. The only requirement is that the gas be exposed to a gas permeable section of flowpath long enough to insure mixture with enough water vapor to achieve the desired degree of humidification. The physical form is not critical. None the less, formation of the gas permeable flowpath by compressing and bonding a layer of open-celled material to water impermeable outer layers at least one of which is gas permeable offer distinct functional and cost advantages including the advantage that those flowpath materials may be readily bonded to materials that are well suited for the construction of the water container and flow port structures. One of the other special features of the invention is that it permits construction of humidifiers with materials that are flexible to the point of being pliant. That simplifies problems in packaging, storage, mounting and disposal.

In accordance with the rules, the best mode now known for practicing the invention has been shown in the accompanying drawing and described in the specification above. However, it is to be understood that other embodiments and variations of the invention are possible and that the invention is to be limited by what is defined in the appended claims rather than by what has been shown.

I claim:

1. In a humidifier for humidifying respiratory gas, the structure comprising:
    a flexible, gas tight bag comprising a front wall and back wall of pliable material bonded together at a marginal bond;
    a labyrinth means having an inlet and an outlet and suspended within said bag and comprising:
    a rear layer porous to water vapor but not to water;
    a front layer porous to water vapor but not to water;
    an intermediate foam layer porous to water vapor;
    bond line means for forming a flow path through said labyrinth means between said inlet and said outlet; and
    bond line means for providing a first passage way between said inlet and the exterior of said bag and a second passageway between said outlet and the exterior of said bag.

2. The humidifier of claim 1 wherein pliable material comprises pliable plastic.

3. The humidifier of claim 2 wherein said rear layer and said front layer comprise Teflon.

4. The invention defined in claim 1 further including anticollapse means for preventing collapse of said flow path under pressure of water resident in said bag.

5. The invention in claim 1 in which said anticollapse means comprises means for rendering turbulent any flow of respiratory gas through said flow path.

6. The invention defined in claim 5 further comprising means for reacting exothermally with water disposed in said bag for heating said water.

* * * * *